US00PP15961P2

(12) United States Plant Patent
Laviana

(10) Patent No.: US PP15,961 P2
(45) Date of Patent: Sep. 13, 2005

(54) ***HOSTA* PLANT NAMED 'GRAND MARQUEE'**

(50) Latin Name: ***Hosta* hybrid**
Varietal Denomination: Grand Marquee

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 109 days.

(21) Appl. No.: 10/809,724

(22) Filed: Mar. 25, 2004

(51) Int. Cl.[7] ..... A01H 5/00
(52) U.S. Cl. ..... Plt./353
(58) Field of Search ..... Plt./353

*Primary Examiner*—Kent Bell
*Assistant Examiner*—Louanne Krawczewicz Myers
(74) *Attorney, Agent, or Firm*—Penny J. Aguirre

(57) ABSTRACT

A new cultivar of hybrid *Hosta*, 'Grand Marquee', characterized by its unique variegated foliage with wide blue-green margins and creamy white centers, its upright, mounding and relatively compact plant habit, and pale lavender flowers positioned above the foliage on strong and erect flower scapes.

2 Drawing Sheets

Botanical classification: *Hosta* hybrid.
Cultivar designation: 'Grand Marquee'.

BACKGROUND OF THE INVENTION

The present invention, *Hosta* 'Grand Marquee', relates to a new and distinct cultivar of *Hosta*, botanically known as a *Hosta* hybrid, hereinafter referred to as 'Grand Marquee'.

The inventor discovered the new cultivar, 'Grand Marquee', in a block of *Hosta* 'Carder Blue' (unpatented) at his nursery in Kensington, Conn. in the summer of 1997. 'Grand Marquee' is a naturally occuring whole plant mutation of 'Carder Blue'. 'Grand Marquee' was selected as unique for its variegated leaf pattern of wide blue-green margins surrounding white centers and its smaller overall plant size in comparison to 'Carder Blue'. 'Carder Blue' has foliage that is blue-green in color and non-variegated.

Asexual reproduction of the new cultivar was first accomplished by in vitro propagation in Kensington, Conn. in the spring of 2001. Asexual reproduction of the new cultivar by division and tissue culture has shown that the unique features of 'Grand Marquee' are stable and reproduced true to type in successive generations.

SUMMARY OF THE INVENTION

The following traits have been repeatedly observed and represent the characteristics of the new cultivar. These attributes in combination distinguish 'Grand Marquee' as a new and unique cultivar of *Hosta*.

1. 'Grand Marquee' has variegated foliage with wide medium blue-green margins and centers that emerge bright green, change to a creamy yellow, and finally change to a creamy white as the leaves mature. An intermediate area, bright green in color exists between the center and margins. The parental plant, 'Carder Blue', is non-variegated.
2. The foliage of 'Grand Marquee' exhibits a heavy substance but lacks the heavily rugose and cupped nature of the leaves of 'Carder Blue'.
3. 'Grand Marquee' reaches a height of about 30 cm (12 in) and a spread of about 64 cm (25 inches) at maturity.

'Carder Blue' reaches a height of about 96 cm (38 in) and a spread of about 45 cm (18 in).

4. 'Grand Marquee' blooms for about 3 to 4 weeks in late summer with pale lavender flowers on scapes about 38 to 43 cm (15 to 17 in) in height.

BRIEF DESCRIPTION OF THE DRAWING

The accompanying colored photographs illustrate the overall appearance and distinct characteristics of the new *Hosta*. The photographs were taken of mature plants of 'Grand Marquee' as grown outdoors in Kensington, Conn.

Figure One was taken in June and provides an overall view of new cultivar.

The photograph in Figure Two is of a close-up view of the flowers of 'Grand Marquee' and was taken in August.

The colors in the photographs are as close as possible with the photographic and printing technology utilized. The color values cited in the detailed botanical description accurately describe the colors of the new *Hosta*.

DETAILED BOTANICAL DESCRIPTION OF THE PLANT

The following is a detailed description of 4 year-old plants of the new cultivar as grown outdoors in Kensington, Conn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Grand Marquee' is a cultivar of *Hosta* of hybrid origin.
Parentage: Naturally occurring whole plant mutation of *Hosta* 'Carder Blue' (not-patented).
General description:
*Blooming period*.—About 3 to 4 weeks in late summer.

*Plant habit.*—Herbaceous perennial. Clump-forming, upright vase-shaped, mounded foliage of medium size.

*Height and spread.*—Reaches about 30 cm in height (about 38 to 43 cm in bloom) and about 64 cm in width.

*Hardiness.*—Zone 3–8.

*Culture.*—Light shade to medium shade, Moist soils of moderate fertility.

*Diseases and pests.*—No susceptibility or resistance to diseases or pests has been observed for 'Grand Marquee'. Thick substance of leaves may confer slug resistance.

*Root description.*—Freely branched, fleshy.

*Propagation.*—In vitro propagation is the preferred method utilizing typical methods for *Hosta*, division are also possible.

*Root development.*—Rooted transplants from tissue culture fully develop in a 32-cell liner in about 6 to 8 weeks in a greenhouse with average temperatures of about 70° F.

*Growth rate.*—Moderate.

Foliage description:

*Leaf shape.*—Ovate when young, becoming broadly ovate when mature.

*Leaf division.*—Simple.

*Leaf base.*—Cordate when mature, more rounded on younger leaves.

*Leaf apex.*—Cuspidate.

*Leaf venation*—About 11 pairs of veins. Camptodrome pattern.

*Leaf margins.*—Entire.

*Leaf attachment.*—Petiolate.

*Leaf arrangement.*—Basal, radiate spirally from base.

*Leaf orientation.*—Held horizontal or at a slight upward angle on petioles held upright at an angle about 60 to 80°.

*Leaf surface.*—Upper and lower: Glaucous.

*Leaf color.*—Young leaves (upper surface): Centers N144A, margins 147A, intermediate area 147B. Young leaves (lower surface): Centers N144B. margins 147B, intermediate area 147C. Mature leaves (upper surface): Centers 155A, margins 146A, intermediate area 144B. Mature leaves (lower surface): Centers 150D, margins 146B, intermediate area 146C.

*Leaf variegation pattern.*—For mature leaves, the center area is on average about 3.5 cm in width comprising about 15 to 30° of the leaf area. The intermediate area is primarily on the border between the center and the margins, is irregular in presence and pattern, and comprises about 5 to 10° of the leaf area.

*Leaf size.*—Up to about 15 to 17 cm in length, up to about 7 to 13 cm in width.

*Leaf quantity.*—About 5 to 7 per shoot (eye).

*Petiole size.*—12 to 22 cm in length, about 0.75 to 1 cm in width narrowing to about 0.5 cm in width at leaf blade attachment.

*Petiole color.*—144A.

*Petiole shape.*—Sulcate.

Flower scape description:

*Scape shape.*—Round, solid.

*Scape number.*—One per mature eye under normal growing conditions.

*Scape posture.*—Straight, held upright at about 80 to 90° from horizontal.

*Scape size.*—About 38 to 43 cm in length, about 5 mm in width and tapering to 1 mm at apex.

*Scape color.*—144A and blushed with shadings of N82C throughout.

*Scape surface.*—Glaucous.

*Leaf bracts (sterile).*—1 to 2 per scape, 142D in color with some variegated of 147A and overlaid with N92A in basal area, ovate in shape, about 1.5 to 2.0 cm in length and 1.5 cm in width.

*Flower bracts (fertile).*—1 per flower, ovate, 142D in color with shadings of N82C, about 1.5 to 2.5 cm in length and about 1.5 cm in width.

Flower description:

*Inflorescence type.*—Terminal racemes on elongated flower scapes.

*Lastingness of inflorescence.*—About 3 to 4 weeks from first opening bloom to fading of last opening bloom, individual blooms last about one week.

*Flower shape.*—Bell-shaped (campanulate-tubular).

*Flower fragrance.*—None detected.

*Flower number.*—About 30 per scape.

*Flower bud shape.*—Spathulate.

*Flower bud size.*—Up to 5 cm in length and about 1.8 cm in width.

*Flower bud color.*—Background color of N155B with markings of N82C to N82D, overall color is lavender, mostly closely represented by 76B.

*Flower size.*—Fully open: About 6 cm in length and about 3 cm in diameter, tube region is about 2.5 cm in length and about 0.5 cm in diameter, expanded region is about 3.5 cm in length and 3 cm in diameter.

*Pedicels.*—About 1.5 mm in diameter, 2.5 mm in length, 144A in color.

*Perianth.*—Comprised 6 Tepals, 3 interior and 3 exterior, overlapping in expanded region and fused in tube region.

*Tepals.*—Background color of N155B with markings of N82D, overall color is light lavender in color 76C on upper and lower surfaces, about 5 to 6 cm in length, about 1.5 cm in width, acute apex, entire margins, spatulate shape, and glabrous texture.

Reproductive organs:

*Gynoecium.*—1 Pistil, style is 1.5 mm in width and exserted up to 1.5 cm beyond tepals, stigma is 1-lobed and 9D in color. Ovary is compound and composed of 3 locules.

*Androcoecium.*—6 stamens, 1 mm in width and exserted up to 1 cm beyond tepals, filament is 150D in color, anthers have versatile attachment and 86C in color, pollen is abundant and 21C in color.

*Seed.*—Seed development has not been observed.

It is claimed:

1. A new and distinct cultivar of *Hosta* plant named 'Grand Marquee' as herein illustrated and described.

* * * * *

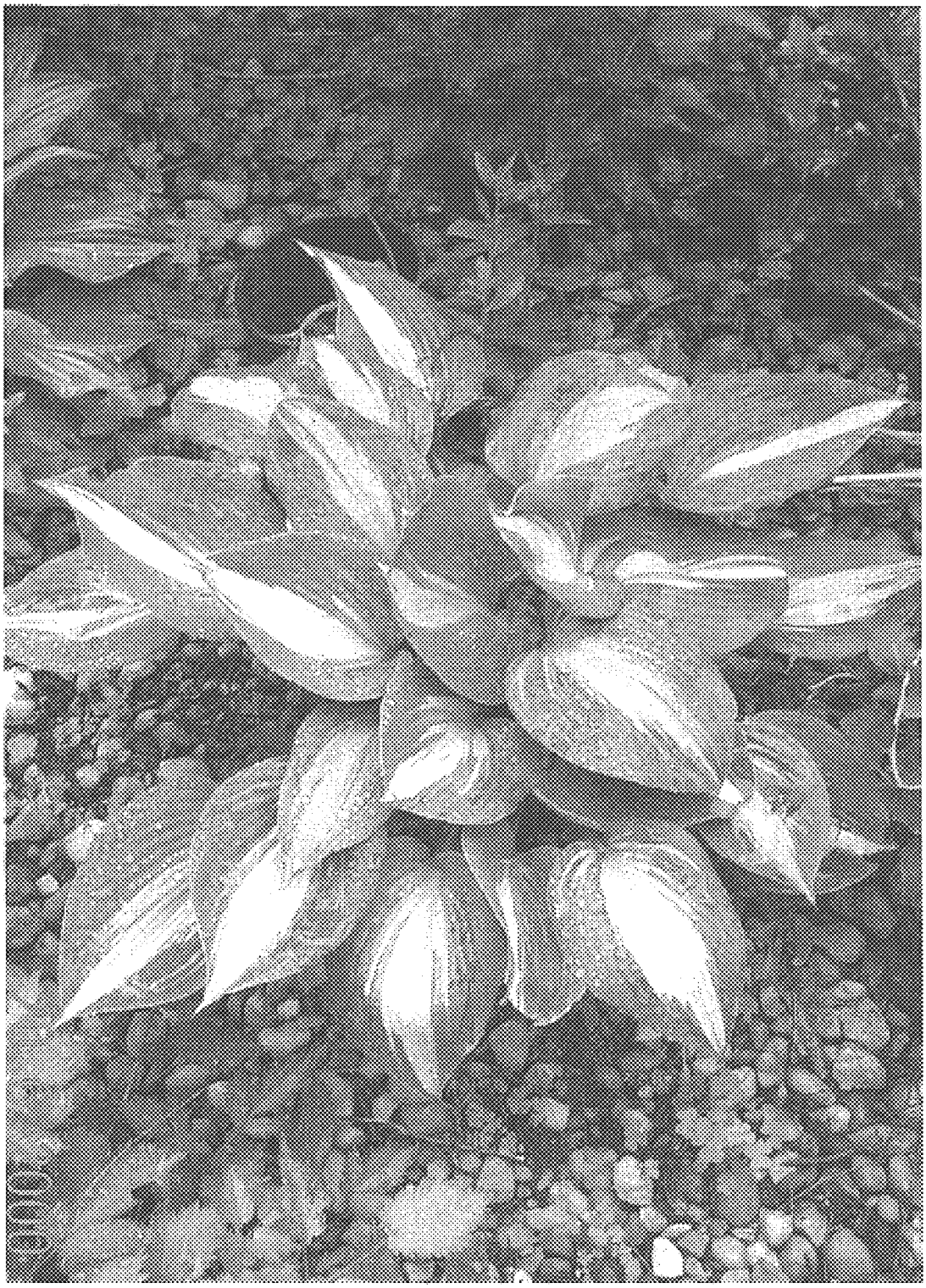
Figure One

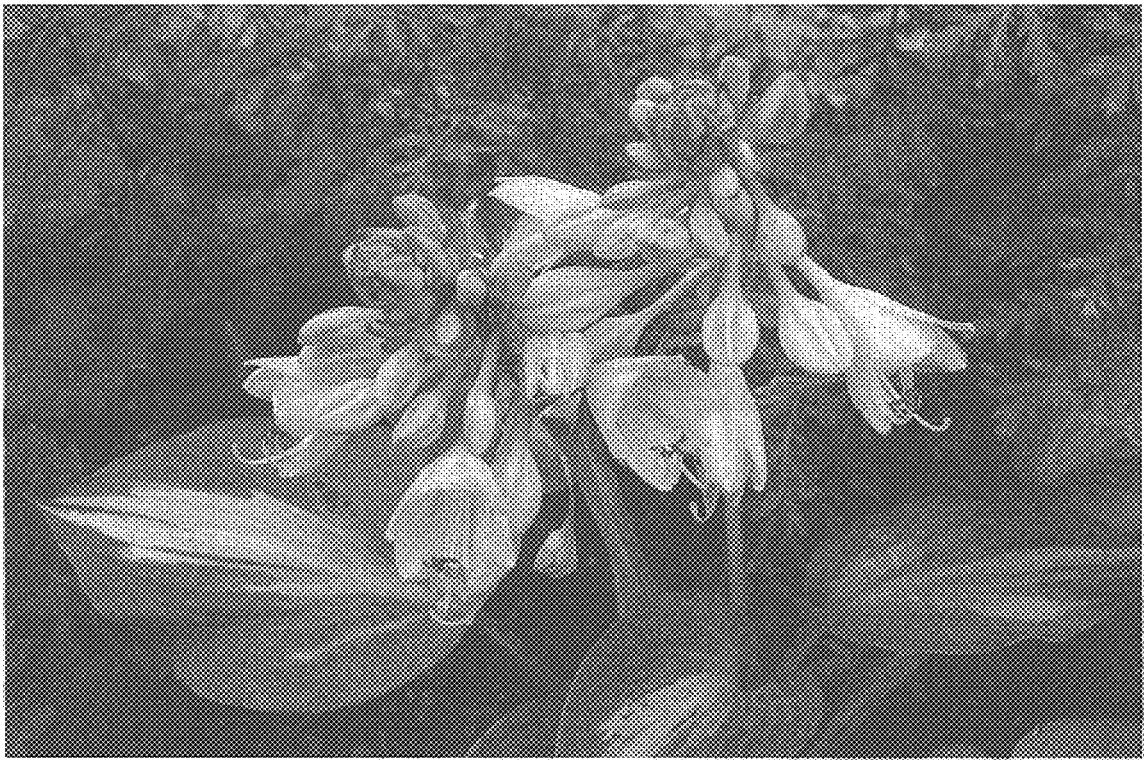
Figure Two